(12) United States Patent
Cheung et al.

(10) Patent No.: US 8,431,090 B2
(45) Date of Patent: Apr. 30, 2013

(54) MICROFLUIDIC DEVICE FOR COUNTING BIOLOGICAL PARTICLES

(75) Inventors: Yuk Kee Cheung, New York, NY (US); Samuel K. Sia, New York, NY (US); Curtis D. Chin, New York, NY (US); Neha Agarwal, Los Altos Hills, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 220 days.

(21) Appl. No.: 12/594,176

(22) PCT Filed: Jun. 30, 2008

(86) PCT No.: PCT/US2008/068869
§ 371 (c)(1), (2), (4) Date: Mar. 8, 2010

(87) PCT Pub. No.: WO2009/006456
PCT Pub. Date: Jan. 8, 2009

(65) Prior Publication Data
US 2011/0243790 A1    Oct. 6, 2011

Related U.S. Application Data

(60) Provisional application No. 60/947,384, filed on Jun. 29, 2007, provisional application No. 60/947,345, filed on Jun. 29, 2007.

(51) Int. Cl.
*B01L 3/00* (2006.01)
*G01N 1/10* (2006.01)

(52) U.S. Cl.
USPC .......... 422/503; 422/500; 422/501; 422/502; 422/504; 422/505; 436/180

(58) Field of Classification Search .......... 422/500–507; 436/180
See application file for complete search history.

(56) References Cited

U.S. PATENT DOCUMENTS

| | | |
|---|---|---|
| 6,432,630 B1 | 8/2002 | Blankenstein |
| 6,632,619 B1 | 10/2003 | Harrison et al. |
| 6,632,652 B1 | 10/2003 | Austin et al. |
| 6,767,706 B2 * | 7/2004 | Quake et al. ................ 435/6.13 |
| 6,936,167 B2 | 8/2005 | Hobbs et al. |
| 6,942,771 B1 | 9/2005 | Kayyem |
| 7,157,049 B2 | 1/2007 | Valencia et al. |
| 7,312,085 B2 | 12/2007 | Chou et al. |
| 7,422,669 B2 | 9/2008 | Jacobson et al. |
| 7,452,725 B2 | 11/2008 | Leary et al. |

(Continued)

OTHER PUBLICATIONS

Balakrishnan, P. et al., "An Inexpensive, Simple, and Manual Method of CD4 T-Cell Quantitation in HIV-Infected Individuals for Use in Developing Countries", Jaids—Journal of Acquired Immune Deficiency Syndromes (2004), vol. 36, 5: pp. 1006-1010.

(Continued)

*Primary Examiner* — Dean Kwak
(74) *Attorney, Agent, or Firm* — Mark A. Catan; Miles & Stockbridge P.C.

(57) ABSTRACT

A particle counter for analyzing blood has features which provide for automatic operation and preferably, also provide for portable use in a low resource setting. In a preferred embodiment, preferred embodiment, the device is used to obtain CD4 counts for AIDS diagnosis.

14 Claims, 3 Drawing Sheets

U.S. PATENT DOCUMENTS

| | | | |
|---|---|---|---|
| 8,008,032 | B2 | 8/2011 | Forsyth et al. |
| 8,071,051 | B2 | 12/2011 | Padmanabhan et al. |
| 8,071,054 | B2 | 12/2011 | Oh et al. |
| 8,168,139 | B2 | 5/2012 | Manger et al. |
| 2004/0253744 | A1 | 12/2004 | Rife et al. |
| 2005/0136548 | A1* | 6/2005 | McDevitt et al. ............. 436/180 |
| 2007/0077605 | A1 | 4/2007 | Hurt et al. |
| 2007/0298433 | A1 | 12/2007 | Sia et al. |
| 2008/0241962 | A1 | 10/2008 | Wang |

OTHER PUBLICATIONS

Ceriotti, L. et al., "An Integrated Fritless Column For On-Chip Capillary Electrochromatography with Conventional Stationary Phases," Analytical Chemistry (2002), 74: pp. 639-647.

Cheng, X. et al., "A Microfluidic Device for Practical Label-Free CD4(+) T Cell Counting of HIV-Infected Subjects," Lab on a Chip, Feb. 2007, 7(2):170-178.

Li, JJ. et al., "Application of Microfluidic Devices to Proteomics Research—Identification of Trace-Level Protein Digests and Affinity Capture of Target Peptides," Molecular & Cellular Proteomics(2002) pp. 157-168.

Mandy, F.F. et al., "Guidelines for Performing Single Platform Absolute CD4+ T-Cell Determinations with CD45 Gating for Persons Infected with Human Immunodeficiency Virus," Centers for Disease Control and Prevention. MMWR Recomm Rep (2003), vol. 52: pp. 1-18.

Mwaba, P. et al., "Use of Dried Whole Blood Spots to Measure CD4+ Lymphocyte Counts in HIV-1-Infected Patients," Lancet (2003) 362: pp. 1459-1460.

Rodriguez, W.R. et al., "A Microchip CD4 Counting Method for HIV Monitoring in Resource-Poor Settings," *PLoS Medicine*, Jul. 2005, 2(7):663-672.

Shapiro, H.M. et al., "Dried Blood Spot Technology for CD4+ T-Cell Counting," Lancet (2004), 363: pp. 164-165.

Andersson H. et al., "Micromachined Flow-Through Filter-Chamber for Chemical Reactions on Beads," Sensors and Actuators B-Chemical (2000), vol. 67, Issues 1-2: pp. 203-208.

Bi XQ et al., "Modified Dynabeads Method for Enumerating CD4+T-Lymphocyte Count for Widespread Use in Resource-Limited Situations", Jaids—Journal of Acquired Immune Deficiency Syndromes (2005), vol. 38: pp. 1-4.

Chin C. et al., Lab-on-a-chip devices for Global Health: Past Studies and Future Opportunities. Lab Chip, Jan. 7, 2000(1): pp. 41-57.

Kannangai R. et al., "Peripheral CD4 +/CD8 + T-Lymphocyte Counts Estimated by an Immunocapture Method in the Normal Healthy South Indian Adults and HIV Seropositive Individuals", J Clin Virol (2000) 17: pp. 101-108.

Mishra NN et al., "On-Chip Micro-Biosensor for the Detection of Human CD4+ Cells Based on AC Impedance and Optical Analysis", Biosens Bioelectron (2005), vol. 21: pp. 696-704.

Oleschuk RD et al., "Trapping of Bead-Based Reagents within Microfluidic Systems: On-Chip Solid-Phase Extraction and Electrochromatography", Analytical Chemistry (2000), 72: pp. 585-590.

Pattanapanyasat K. et al., "CD4+ T Cell Count as a Tool to Monitor HIV Progression & Anti-Retroviral Therapy", Indian Journal of Medical Research (2005), 121: pp. 539-549.

Sato K. et al., "Integration of an Immunosorbent Assay System: Analysis of Secretory Human Immunoglobulin A on Polystyrene Beads in a Microchip", Analytical Chemistry (2000), 72: pp. 1144-1147.

Unger et al., "Monolithic Microfabricated Valves and Pumps by Multilayer Soft Lithography," *Science*, 2000, 288(5463):113-116.

Wang C. et al., "Integration of Immobilized Trypsin Bead Beds for Protein Digestion within a Microfluidic Chip Incorporating Capillary Electrophoresis Separations and an Electrospray Mass Spectrometry Interface", Rapid Communications in Mass Spectrometry (2000), 14: pp. 1377-1383.

Bhattacharyya et al., "Design and Testing of a Disposable Microfluidic Chemiluminescent Immunoassay for Disease Biomarkers in Human Serum Samples," Biomedical Microdevices, 2007, 9:pp. 245-251.

Lv et al., "Chemiluminescence Microfluidic System Sensor on a Chip for Determination of Glucose in Human Serum with Immobilized Reagents," Talanta, 2003, 59:pp. 571-576.

Xiang et al., "Miniaturized Immunoassay Microfluidic System with Electrokinetic Control," Biosensors and Bioelectronics, Apr. 2006, 21(1):pp. 2006-2009.

Yakovleva et al. "Microfluidic Enzyme Immunoassay Using Silicon Microchip with Immobilized Antibodies and Chemiluminescence Detection," Analytical Chemistry, 2002, 74:pp. 2994-3004.

\* cited by examiner

MICROFLUIDIC DEVICE FOR COUNTING BIOLOGICAL PARTICLES

CROSS REFERENCE TO RELATED APPLICATIONS

The present application is a US National Stage, application of PCT/US08/68869 filed Jun. 30, 2008, which claims priority to US Provisional Applications 60/947,384 and 60/947,345, which were both filed Jun. 29, 2007, entitled "Microfluidic Device for Counting Cells" hereby incorporated by reference in their entireties herein

BACKGROUND

Practical HIV diagnostics are urgently needed in resource-limited settings. While HIV infection can be diagnosed using simple, rapid, lateral flow immunoassays, HIV disease staging and treatment monitoring require accurate counting of a particular white blood cell subset, the CD4(+) T lymphocyte.

Current systems for providing this function are expensive, technically demanding and/or time-consuming. For example, CD4 counts may be obtained by conventional flow cytometry. The method requires a slow flow rate to capture the cells on the surface of the channel, followed by a quick wash. This is not easy to implement in a point-of-care device, where the fluid actuation technique must be fairly simple. They require a microscope and a camera (or a person) to count the captured cells. This method is suitable for a lab environment, not point of care.

SUMMARY

According to an embodiment, the invention is a portable microfluidic device for counting CD4+ T-cells. In a method embodiment, the device is used to count CD4+ T-cells and the information from the counting is used as a key diagnostic criterion for determining whether to administer antiretroviral therapy to HIV-infected patients. In the device embodiment, a disposable microfluidic cassette contains densely packed beads for capturing T-cells. A portable, self-powered instrument operatively associated with the microfluidic cassette reads and displays the result of the counting. Preferably, the device employs bead-based microfluidics to enhance surface area for cell capture. For example, in an embodiment, a "double-dam" design is employed which is compatible with whole blood. Preferably, a small pump is employed to permit complete compactness and low power requirement. Also, preferably, the device uses a portable detection device based on an absorbance/chemiluminescence reader. In a particularly preferred embodiment, the detector is powered by a solar batter, which can, for example facilitate its use in point-of-care settings in the developed countries, as well as developing countries.

In a particular variation, the device uses cell affinity chromatography operated under differential shear flow to specifically isolate CD4(+) T lymphocytes. In an embodiment, the device may be effective with a direct processing of 10 microliters of unprocessed, unlabeled whole blood. CD4 counts are, in this embodiment, obtained under an optical microscope in a rapid, simple and label-free fashion. For example, the embodiments are effective for a range of absolute CD4 counts ($R(2)=0.93$) over which the embodiments are operable. This CD4 counting microdevice can be used for simple, rapid and affordable CD4 counting in point-of care and resource-limited settings.

In a preferred configuration, packed beads are provided in a microchannel to enhance capture surface area which increases the cell-capture efficiency to enhance the final signal, and allows constant flow, permitting the use of a small pump, preferably peristaltic and preferably powered by a battery. Preferably, capture and detection are done in the same location. Optics are employed that automatically reads the signal either by absorbance or chemiluminescence or some other suitable technique. The optical components are preferably portable and as such, are, in the preferred embodiment, powered by battery including the detection portion, the pumping portion, and the microfluidic channel chip. Preferably, rechargeable batteries are used.

A portable blood component analysis device has a microfluidic unit with a sample chamber defined in a first longitudinal channel having a first major axis and a second longitudinal channel, having a second major axis, in communication with the first longitudinal channel with the second major axis crossing the first major axis; the sample chamber having a surface augmentation features with biospecific surface configured to capture particles from blood; an analyzer component having a signal detector and a receiving slot configured to receive the microfluidic unit and align the sample chamber with the signal detector. Preferably, the first and second major are substantially perpendicular. Preferably, the analyzer contains a pump configured to generate a vacuum of at least 10 kPa. Preferably, the surface augmentation features include a packed bead bed with glass beads. Preferably, the surface augmentation features include a packed bead bed with glass beads with a diameter between 50 and 100 µm and the first longitudinal channel contains a narrow portion with a minimum dimension of less than the diameter of the glass beads. Preferably, the device further includes a pump, a controller and a solar power source connected to power the pump and controller. Preferably, the microfluidic unit includes a tube containing at least one, at least one wash, and at least one air bubble, the tube being reversibly sealed at both ends and configured to connect with the second longitudinal channel. Preferably, the device further includes a pump, a controller and a solar power source connected to power the pump and controller, wherein the microfluidic unit includes a tube containing at least one, at least one wash, and at least one air bubble, the tube being reversibly sealed at both ends and configured to connect with the second longitudinal channel and wherein the controller is configured automatically to pump fluids from the tube through the sample chamber and through the second longitudinal channel. In any of these devices, the blood particles detected may include CD4 cells. Preferably, a battery is included. Preferably, a controller receives a signal from the signal detector and the signal is a light intensity, the controller being configured to derive a cell count from a light intensity signal without imaging. Preferably, the controller is configured to derive the cell count from a calibration lookup table correlating cell count against total light intensity from the sample chamber.

Another portable blood component analysis device has a microfluidic unit with a sample chamber; the sample chamber having a surface augmentation features with biospecific surface configured to capture particles from blood; an analyzer component having a signal detector and a receiving slot configured to receive the microfluidic unit and align the sample chamber with the signal detector; Preferably, the surface augmentation features include a packed bead bed with glass beads. The device claim 13, wherein the analyzer contains a pump configured to generate a vacuum of at least 10 kPa;. Preferably, the surface augmentation features include a packed bead bed with glass beads with a diameter between 50 and 100 μm and the first longitudinal channel contains a narrow portion with a minimum dimension of less than the diameter of the glass beads. Preferably, the device includes a controller and a solar power source connected to power the pump and controller. Preferably, the microfluidic unit includes a tube containing at least one, at least one wash, and at least one air bubble, the tube being reversibly sealed at both ends and configured to connect with the second longitudinal channel. Preferably, the device has a pump, a controller and a solar power source connected to power the pump and controller, wherein the microfluidic unit includes a tube containing at least one, at least one wash, and at least one air bubble, the tube being reversibly sealed at both ends and configured to connect with the second longitudinal channel and wherein the controller is configured automatically to pump fluids from the tube through the sample chamber and through the second longitudinal channel. Preferably, the blood particles include CD4 cells. Preferably, the device has a battery powered by solar power source. Preferably, the device has a controller and the signal detector is a light intensity detector and the controller is configured to derive a cell count from a light intensity signal without imaging. Preferably, the controller is configured to derive the cell count from a calibration lookup table correlating cell count against total light intensity from the sample chamber. Preferably, the device has a display configured to output a cell count. Preferably, the device has a controller and the signal detector is a light intensity detector and the controller is configured to derive a cell count from a light intensity signal without imaging. The device of claim 23, wherein the controller is configured to derive the cell count from a calibration lookup table correlating cell count against total light intensity from the sample chamber. Preferably, the device includes a pump, a controller and a solar power source connected to power the pump and controller, wherein the microfluidic unit includes a tube containing at least one, at least one wash, and an a chemiluminescence activator, the tube being reversibly sealed at both ends and configured to connect with the second longitudinal channel and wherein the controller is configured automatically to pump fluids from the tube through the sample chamber and through the second longitudinal channel.

Preferably, the pump is controlled to vary a pumping rate depending on a sample or reagent passing through the sample chamber.

DETAILED DESCRIPTION OF EMBODIMENTS

Figure 1:
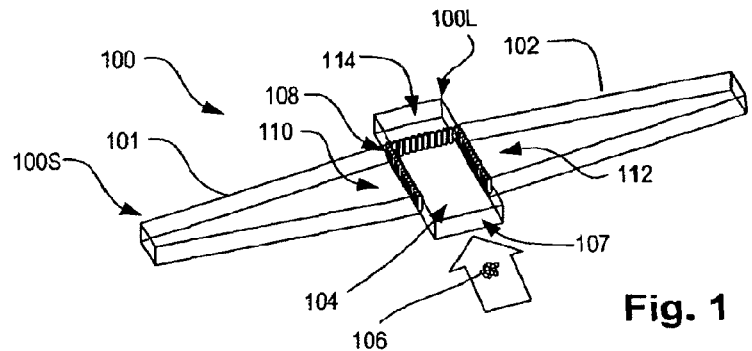
FIG. 1 shows a first embodiment of a sample analyzer.

Referring to FIG. 1, a T-shaped microfluidic device 100 has a sample channel 100S for sample fluid and reagents and a loading channel 100L for loading particles that providing surface augmentation, such as glass or polystyrene beads 106. The particles preferably carry immobilized biospecific molecules or other reactive substances on their surfaces. An inlet channel 101 and an outlet channel 102 are used to convey a sample fluid, such as blood, and reagents and washes through the sample channel 100S. The loading channel 100L is used to fill a chamber 104 with the surface augmentation particles to form a packed bed within the chamber 104. The beads 106 are trapped in a cage made up of microposts 108 defining sample inlet, sample outlet fences 110, 112, and 114. The beads may be suspended in a fluid and conveyed through a loading port 107 along with the fluid suspending them into the chamber 104 while permitting the fluid to drain through gaps between the posts 108. The beads may be loaded in by flowing them in a suspension by pumping a fluid into the bed 104 area and drawing excess carrying fluid out through a fence 114 trapping the beads 106 in the bed 105 and packing them with a repeatable density.

Preferably, the gap between the posts is smaller than the breads. The Posts 108 can be many times the size of the beads. The beads do not have to be a constant size, but preferably they are a consistent size to help ensure a packing arrangement with a large and predictable void volume. If desired, a step may be added, for example, to coat the bead particles with a stabilizing or protecting material.

Although not shown in the drawing, the chamber 104 is enclosed at the top and bottom. The entire structure can be made using lithographic techniques that are well known. Once packed with the surface augmenting particles, loading channel 100L can be permanently sealed at both ends and the sample channel 100S temporarily sealed for storage and/or shipping. The device 100 may be combined with multiple such devices 100 on a single piece of substrate, each with a bed having a different immobilized biospecific substances to permit detection of different sample fluid components. In use, the sample channel 100L is unsealed such that fluid can enter and leave chamber 104 through the inlet and outlet channels 101 and 102. The drawing does not show the beads 106 in place in the bead bed 104.

Figure 2A:
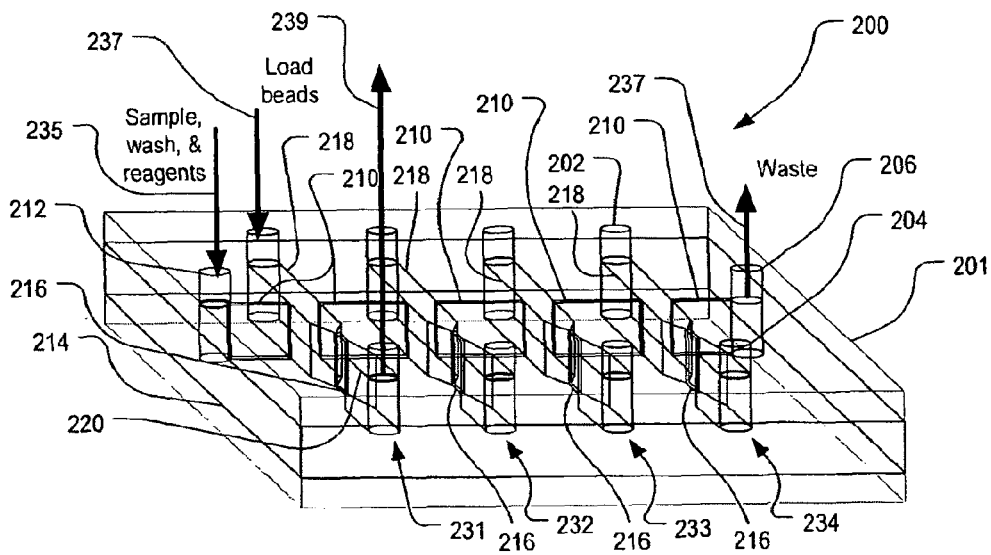
FIGS. 2A and 2B show a second embodiment of a sample analyzer.
Figure 2B:
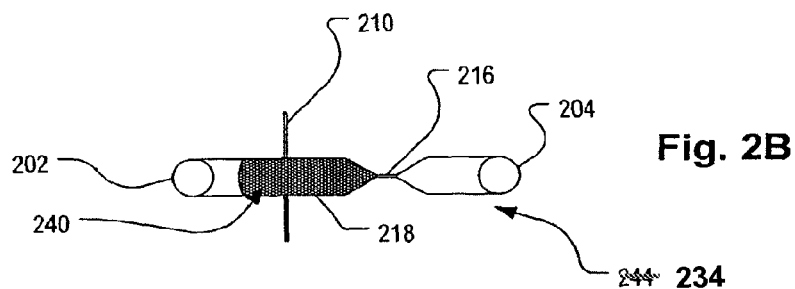

Referring to FIGS. 2A and 2B, an array of sample channels 231, 232, 233, and 234, each having a sample chamber 218, is formed in a substrate 201. The sample chambers 218 are functionally similar to the chamber 104 of FIG. 1, except that in the present embodiment, narrow channels 216 are used to retain the surface augmentation particles 106, for example, beads. The beads are loaded into loading ports 202 (as indicated by arrow 237—only one port 202 is labeled to avoid crowding the drawing, but the others are similarly configured). The beads are held back by the narrow channels 216 and the fluid carrying the beads exits as shown by the arrow 239 out of an exit port 204. Using these structures, beads with different immobilized substances can be loaded in each sample chamber 218. Once the sample chambers 218 are packed, the ports 202 and 204 are sealed and the device 200 can be used or stored and/or shipped. In other respects, the device 200 is similar to that described with reference to FIG. 1.

In use, the sample, washes, and reagents (collectively indicated by arrow 235) are loaded through sample inlet ports 212 and spent fluids recovered or disposed of through sample outlet port 206 (arrow 237). As described below, sample channels 210 convey a fluid train (the sample, washes, and reagents) serially through each of the sample chambers. Preferably, the fluid train is drawn through the device 200 using a vacuum pump regulated to maintain a pressure that provides desired shear rate which has been determined to remove particles that do not bind with the beads (more specifically, the active surface of the bead particles) and permit those particles (such as cells) that do bind to remain in the sample chambers 218. In certain embodiments, it will preferably be determined the range of shear rates that provide the desired discrimination behavior.

FIG. 2B illustrates, as viewed from the top, a single sample chamber 218 with beads 240 packed within. The sample channel 210 permits the train of sample fluid and reagents to pass through. Preferably, the sample line has a size that prevents the migration of substantial quantities of beads 240 from the sample chamber 218. In an embodiment, the sample channel width is selected to be slightly smaller than the coated beads.

As will be described below, sample fluid particles in sample fluid, such as CD4 cells (particles) in blood (sample fluid) flow into the sample chamber followed by a wash, followed by a fluid carrying free signal molecules, followed by a wash, followed by a fluid carrying a free signal amplifier molecule. In each case, a different shear rate may be desirable to ensure that only the reactive particles or molecules are left behind and such that the shear rate is not so high as to interfere with the ability of particles to attach ultimately to the beads or substances thereon. The shear rate may vary depending on the component of the assay, for example, when a wash is applied versus when a reagent is applied. Shear rate may vary for different reagents as well. Preferably, an automated device, as described below, is provided with a controller to vary the total vacuum to vary the shear rate accordingly. This may be synchronized to the stage of the assay by detecting a property of the fluid train (e.g. detecting air bubbles that isolate the fluids from each other), by time after start of the vacuum pump, by detecting momentary changes in the vacuum pressure caused by passage of different fluids, such as air, into the beds, or other means.

Figure 3:
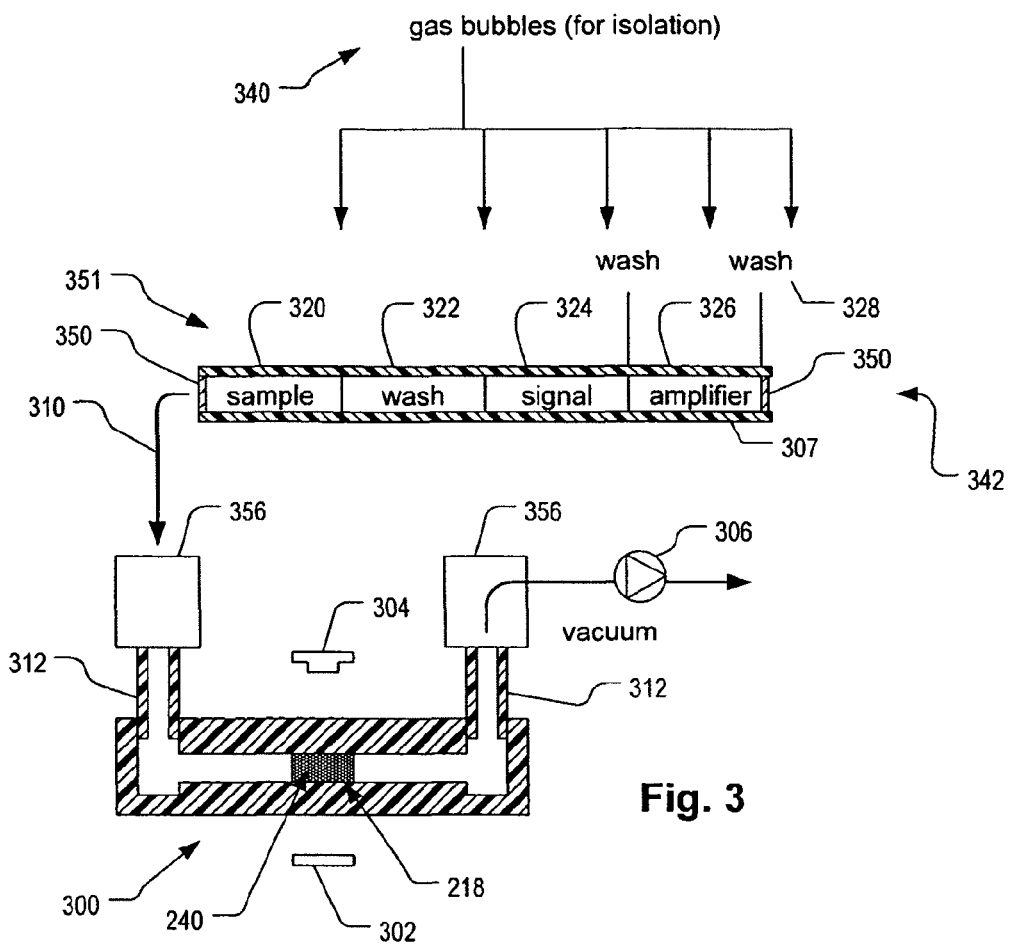
FIG. 3 shows a multiple-chamber sample analyzer showing various features.

Referring to FIG. 3, beads 240 configured for capturing the target cells (such as by anti-target cell antibody) are packed in a bed 218 in an analyzer device 300. The device has tubing 312 with connectors 356 that connect to sample fluid train 351 and a vacuum pump 306. The sample fluid train may be held in a long tube 307 which is sealed with rupturable seals 350. The rupturable seals may be configured to rupture upon application of a vacuum or by being pierced automatically by a sharp edge (not shown) when installed in a portable device. After the sample fluid train passes through the device 300, a signal detector 302 may detect light caused by a reaction, for example, chemiluminescence or fluorescence. In the latter case, a light source, such as photodiode 304 may be provided. In a preferred embodiment, the number of cells captured in the sample chamber is the quantity of interest and preferably the system is configured such that the total amount of light captured by the detector indicates the number of cells according to a predetermined calibration curve stored in a portable controller and the cell count or other indication displayed automatically by the device.

The train of fluid 310 including sample fluid 320, such as whole blood conveyed through an inlet channel 312 to the bed 218. The sample fluid train may include further fluids, each separated from each other, as appropriate in view of their mutual activity, by air or gas bubbles 340. The fluid train may also include washes 322, 328, fluids carrying intermediate materials such as antibodies that bind signal molecules, fluids carrying signal molecules 324, developers and, fluids carrying signal amplifiers 326, etc. For another example, the sample fluid train may include substance that causes chemiluminescence.

In a preferred embodiment, the target that reacts with the reactive substance on the beads is lymphocytes (for example CD4 cells) carried in the sample fluid, blood. In such embodiment, is followed by a wash and then a target cell antibody (the primary antibody). In the principal embodiment, this is a CD4 cell primary antibody; i.e., an antibody that recognizes a CD4 cell. Following that, a quantity of a detectable (labeled) secondary antibody that recognizes the CD4 cell antibody is conveyed through the inlet channel and binds or associates with the primary antibody. A developer may be conveyed as well to enhance or permit detection.

As mentioned, to detect the quantity of target cells retained in the sample chambers, the device preferably measures the strength of an optical signal. Examples included fluorescence, label (e.g. silver) absorbance, and chemiluminescence. Techniques which are known in the prior art, may be employed. A small electronic (charge-coupled device; "CCD") camera, microscope, or other suitable photodetector device can be employed with suitable optics and filtering to provide an indicator signal. The total magnitude of the light signal may be compared to a standard to quantify the count of cells.

In an exemplary embodiment, the embodiments employ dimensions that are determined to permit the close packing in a single layer while permitting sufficient flow of sample fluid and reagents without clogging. The dimensions of the embodiment of FIG. 1 may include 90 µm-diameter microposts 108 spaced apart a distance smaller than the beads 108, for example, spaced 25 µm apart to trap them. The beads are 40 µm-diameter and the depth (dimension parallel to the axes of the microposts 108) of the channel defined by the bed 104 is 75 µm-tall channels. In an exemplary embodiment, the bed 104 is 2 mm by 2 mm. The void fraction of the packed bed 104 may be chosen such that cells clear the column after a few washes.

Figure 4A:
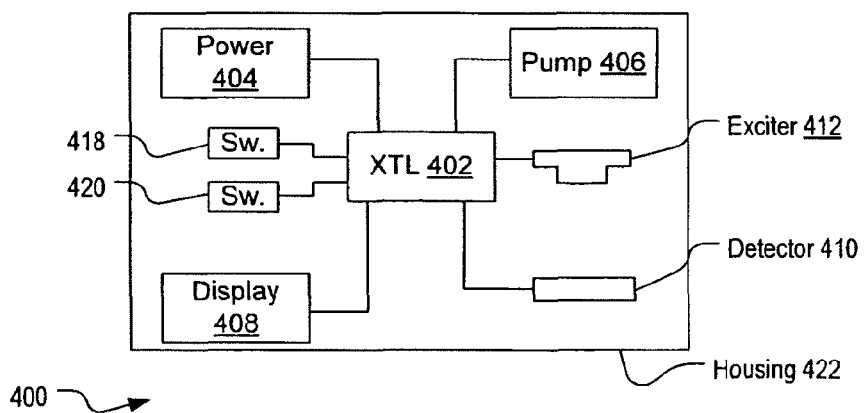
FIGS. 4A, 4B, and 4C illustrate embodiments of portable sample analyzer machines.

Referring to FIG. 4A, a schematic of a portable analyzer 400 has a power source 404, for example, a solar cell or hand generator. A microprocessor based microcontroller (XTL) 402 controls the unit and drives a pump, (optionally, if used) a light source (e.g., laser diode) or other exciter 412, photodetector 410, and a display 408, preferably an LCD. Inputs from a user may be provided by suitable actuators such as membrane switches to allow a user to operate the device. Switches, 418 and 420 may be limited to power on and run functions to make the unit fully automated and simple to operate. A housing 422 is preferably provided to form a unitary portable device.

Figure 4B:
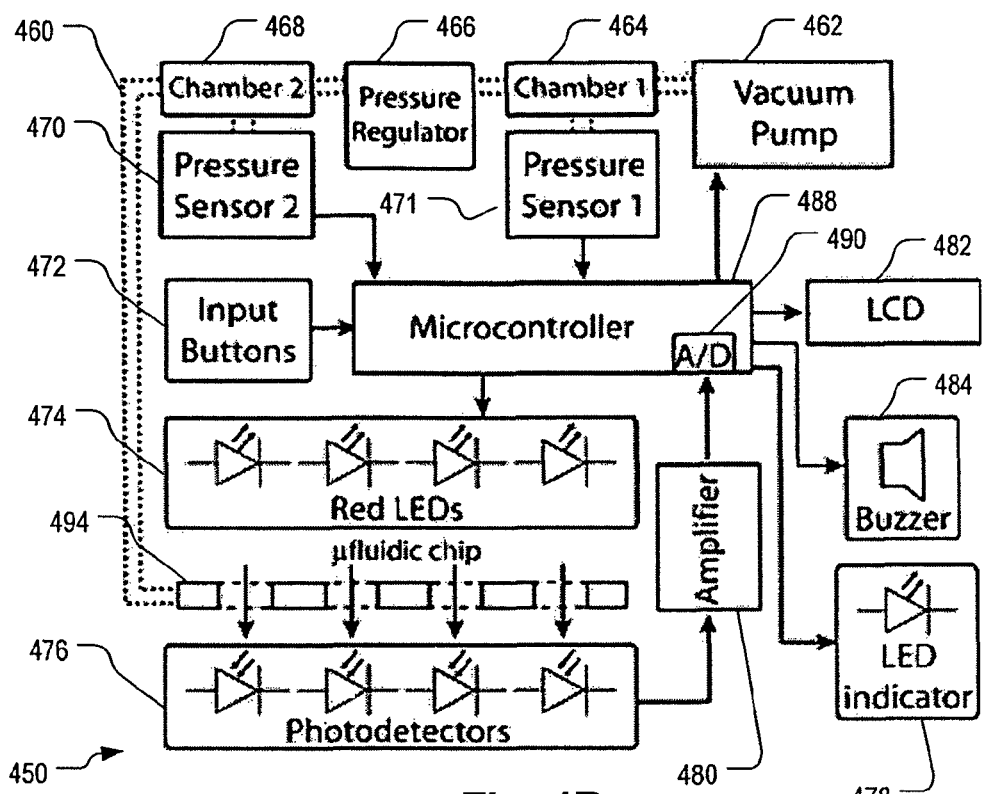

Referring to FIG. 4B, a more detailed embodiment of a portable analyzer 450 has a vacuum pump 462 to generate a vacuum for drawing sample and reagents through a microfluidic chip 494 as discussed above. A pressure sensor 471 detects a pressure signal via a pressure chamber 464 which smooths out pressure pulses, indicating the vacuum output of the vacuum pump. Another pressure sensor 470 detects a pressure signal via a pressure chamber 468 which also smooths out pressure pulses, the latter signal indicating the regulated vacuum pressure determined by a pressure regulator 466. The pressure signals are applied to a microcontroller 488 as are signals from user control actuators 472, and photodetector signals from one or more photodetectors 476 amplified by an amplifier 480. The signal from the photodetectors 476 may are preferably sampled and converted to digital data and processed for analysis to permit results to be displayed on a display 482. Further output devices may include an indicator annunciator 484 and/or an indicator lamp 478. The latter may be used, for example, to indicate the completion of an analysis and the status of the device 450, respectively, for example.

Figure 4C:
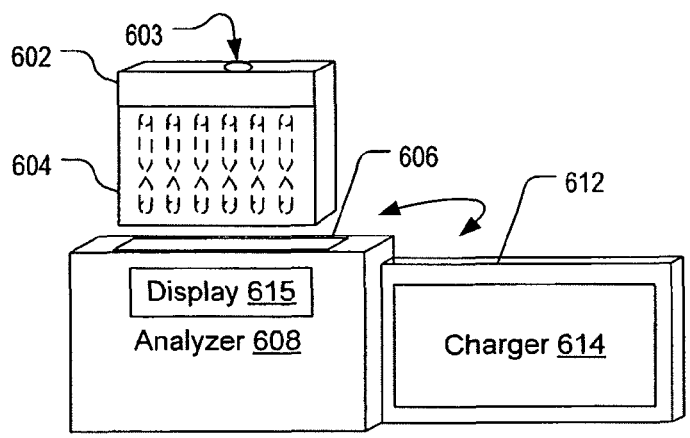

Referring to FIG. 4C, in a preferred embodiment, a microfluidic chip 604 with reagent cache 602 (tube filled with reagent and having a sample port 603) is configured to be received in a recess 606 of an analyzer 608 to form a configuration as described with reference to FIGS. 4A or 4B. In the present embodiment, a swing-out front panel has a solar charger 614. Control buttons such membrane switches (not shown) may be provided on the housing. A circuit board (not shown) carrying an LCD display 615 may be carried on the front panel. The microfluidic channel "chip" 604 (and fluid train cache 602) may be provided in the form of a replaceable component which is used once for each measurement and discarded. In a following layer a circuit board carries a microcontroller and photodetector (or camera or other sensor) positioned to detect light from the bead bed. Batteries and a pump may be carried in a lower chassis. The entire structure shown can be packaged in a hinged device which may be opened to insert the microfluidic chip while permitting access for the drawing of a sample fluid (and any detection or development agents required).

In an exemplary embodiment, the laser diode may, for example, have a wavelength of 654 nm. The device may have an alignment slot, which is exposed when opened, to permit the proper location of the microfluidic chip. It may also have a Polydimethylsiloxane window to protect the detector and/or the light source. In an embodiment, the photodetector records changes in adsorbance, for example due to opacity of a developing silver film. In another embodiment, the photodetector detects light emitted by captured sample material and labels, e.g., by fluorescence. Preferably, results are displayed digitally to minimize subjective interpretation by the user.

To confirm the above configuration, a passive adsorption of antibodies onto beads was tested. The capture of 3T3fibroblasts on the beads (coated with human fibronectin), and CD4 T-cells (using anti-CD4 antibodies) has been demonstrated by experiment. An ability to capture both fibroblasts and lymphocytes with this method (FIG. 2A), has been confirmed. The use of covalent chemistry has been investigated, using carboxylated beads and the carbodiimide coupling agent EDC. Beads coated with anti-CD4 successfully captured T-cells from whole blood of AIDS patients, by DIC (FIG. 2B) and fluorescence microscopy (FIG. 2C). Among commercially available antibodies, it was found that only a small number have strong affinity for CD4 and can be easily coated onto surfaces.

To prepare glass beads, the following methodology was experimentally confirmed as suitable for use in the above embodiments. First, beads having a diameter of about 50 μm were subjected to 2 N nitric acid wash for 1 hour (to clean the glass beads). Next, the beads were silanized with 10% APTES (an aminosilane) overnight at room temperature. The beads were washed with toluene and acetone, and dried in an oven at 60 C for 2 hr. Then the beads were reacted with 2.5% glutaraldehyde (to crosslink terminal –NH2 on APTES with primary amines on proteins added later) for 1 hour at room temperature and subsequently washed with distilled water. The next step was to couple 10 μg/ml of protein G onto silanized glass surface (to orient anti-CD4+ antibody with F(ab) towards mobile phase, and to act as additional spacer). The next step was to wash 3 times with phosphate buffer saline solution and couple 10 μg/ml of mouse-anti-human CD4+ antibody onto protein-G coated glass surface. Specific binding of fluorescent antibodies was demonstrated, using bovine serum albumin (BSA) as a negative control to block binding of fluorescent secondary antibody markers (AF-488 goat anti-mouse antibodies).

It has been experimentally determined that beads of a certain minimum size are preferred to reduce clogging by cell particles. In balancing the size against the reduction in surface, the preferred size range has been determined to be in the range of 50-100 and preferably about 75-80 μm diameter. An exemplary shear rate determined to provide reliable discrimination is 10-20 dyn/cm$^2$.

The invention claimed is:

1. A portable blood component analysis device, comprising:
    a microfluidic unit including:
    a sample chamber defined in a first longitudinal channel having a first major axis and a second longitudinal channel having a second major axis in communication with the first longitudinal channel, with the second major axis crossing the first major axis, the first longitudinal channel being configured to convey blood into and out of the sample chamber, the sample chamber having a surface augmentation features with biospecific surface configured to capture particles from blood, the surface augmentation feature including a plurality of surface augmentation particles or beads loaded into the sample chamber through the second longitudinal channel using a loading fluid; and
    a restraining structure including a plurality of microposts forming a fence-like structure around a portion of the sample chamber and configured to retain the plurality of surface augmentation particles in the sample chamber and allow the loading fluid and the blood to exit the sample chamber through the restraining structure; and
    an analyzer component having a signal detector and a receiving slot configured to receive the microfluidic unit and align the sample chamber with the signal detector.

2. The device of claim 1, wherein the first and second major axis are substantially perpendicular.

3. The device of claim 1, wherein the analyzer includes a pump configured to generate a vacuum in the sample chamber of at least 10 kPa.

4. The device of claim 3, further comprising a battery connected to the pump.

5. The device of claim 1, wherein the surface augmentation features includes glass beads forming a packed bead bed and the restraining structure is configured to keep the glass beads in said packed bead bed configuration in which the plurality of glass beads are in mutual contact.

6. The device of claim 5, wherein a diameter of a glass bead is between 50 and 100 μm.

7. The device of claim 1, wherein the microfluidic unit includes a tube configured to connect with the second longitudinal channel, the tube being further configured to be sealed at both ends, and carry at least one wash fluid and at least one air bubble.

8. The device of claim 1, further comprising a pump, a controller, and a solar power source connected to power the pump and the controller, wherein the microfluidic unit further includes a tube configured to be sealed at both ends and configured to connect with the second longitudinal channel, and wherein the controller is configured automatically to pump fluids from the tube through the sample chamber and through the second longitudinal channel.

9. The device of claim 1, wherein the blood particles include CD4 cells.

10. The device of claim 1, further comprising a controller, wherein the signal detector is a light intensity detector and the controller is configured to derive a cell count from a light intensity signal without imaging.

11. The device of claim 10, wherein the controller is configured to derive the cell count from a calibration lookup table correlating cell count against total light intensity from the sample chamber.

12. The device of claim 1, wherein a gap between each adjacent micropost is smaller than a diameter of the smallest particle in the plurality of particles such that the particles cannot pass through the gaps.

13. The device of claim 12, wherein the plurality of microposts are arranged around three sides of the sample chamber.

14. The device of claim 1, wherein the restraining structure includes narrowed portions of the first and second longitudinal channels, the narrowed portions being the portions of the corresponding first and second longitudinal channels facing the sample chamber, the narrowed portions having sizes that are smaller than a diameter of the smallest particle in the plurality of particles, such that the particles cannot pass through the narrowed portions.

\* \* \* \* \*